(12) United States Patent
Kwon

(10) Patent No.: US 11,185,306 B2
(45) Date of Patent: Nov. 30, 2021

(54) ULTRASOUND PROBE

(71) Applicant: SAMSUNG MEDISON CO., LTD., Gangwon-do (KR)

(72) Inventor: Soon Ho Kwon, Gumi-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 603 days.

(21) Appl. No.: 15/948,683

(22) Filed: Apr. 9, 2018

(65) Prior Publication Data
US 2019/0231311 A1    Aug. 1, 2019

(30) Foreign Application Priority Data

Jan. 31, 2018   (KR) ........................ 10-2018-0011929

(51) Int. Cl.
| | | |
|---|---|---|
| *E21B 47/16* | (2006.01) | |
| *A61B 8/00* | (2006.01) | |
| *A61B 8/08* | (2006.01) | |
| *B06B 1/02* | (2006.01) | |

(Continued)

(52) U.S. Cl.
CPC .......... *A61B 8/4455* (2013.01); *A61B 8/445* (2013.01); *A61B 8/4477* (2013.01); *A61B 8/4494* (2013.01); *A61B 8/5207* (2013.01); *B06B 1/0207* (2013.01); *B06B 1/0607* (2013.01); *B06B 1/067* (2013.01); *B06B 1/0622* (2013.01); *G01N 29/245* (2013.01);

(Continued)

(58) Field of Classification Search
None
See application file for complete search history.

(56) References Cited

U.S. PATENT DOCUMENTS 2,843,823 A  *  7/1958  Bayless .................. G01N 27/07
                                           324/446
5,044,053 A  *  9/1991  Kopel .................... B06B 1/0622
                                           29/25.35

(Continued)

FOREIGN PATENT DOCUMENTS

| JP | S61-107154 A | 5/1986 |
| JP | 2009-247511 A | 10/2009 |
| KR | 10-2002-0091875 A | 12/2002 |

OTHER PUBLICATIONS

Extended European Search Report dated Nov. 21, 2018 issued in European Patent Application No. 18176071.1.

*Primary Examiner* — Yuqing Xiao
*Assistant Examiner* — Jonathan D Armstrong
(74) *Attorney, Agent, or Firm* — Morgan, Lewis & Bockius LLP

(57) ABSTRACT

An ultrasound probe includes a first assembly having a first case, a second assembly coupled with the first assembly, having a second case, and configured to be rotatable between a first position of being unfolded with respect to the first assembly and a second position of being folded on the first assembly, a first acoustic module disposed in the inside of the first case, a second acoustic module disposed in the inside of the second case, and a first space reducing portion disposed in at least one of a portion of the first case toward the second assembly and a portion of the second case toward the first assembly, and configured to reduce a space between the first acoustic module and the second acoustic module when the second assembly is at the first position.

11 Claims, 13 Drawing Sheets

(51) Int. Cl.
*B06B 1/06* (2006.01)
*G01N 29/24* (2006.01)

(52) U.S. Cl.
CPC ..... *G01N 29/2406* (2013.01); *G01N 29/2412* (2013.01); *A61B 8/5253* (2013.01); *B06B 2201/76* (2013.01)

(56) References Cited

U.S. PATENT DOCUMENTS

| | | | | |
|---|---|---|---|---|
| 5,341,810 | A * | 8/1994 | Dardel | A61B 8/0833 600/461 |
| 5,491,651 | A * | 2/1996 | Janik | G06F 1/163 361/679.03 |
| 5,846,196 | A * | 12/1998 | Siekmeyer | A61B 5/0422 600/374 |
| 6,261,237 | B1 * | 7/2001 | Swanson | A61B 7/04 600/527 |
| 6,519,862 | B1 * | 2/2003 | Owsley | A61B 5/103 33/501.02 |
| 8,766,926 | B2 * | 7/2014 | Wirtanen | G06F 3/0346 178/18.01 |
| 9,463,267 | B2 * | 10/2016 | Katsumoto | G06F 3/033 |
| 9,615,473 | B2 * | 4/2017 | Kim | G06F 1/1652 |
| 2002/0002371 | A1 * | 1/2002 | Acker | A61N 7/022 606/27 |
| 2005/0056920 | A1 * | 3/2005 | Li | H01L 24/32 257/686 |
| 2005/0215895 | A1 | 9/2005 | Popp et al. | |
| 2006/0276711 | A1 | 12/2006 | Yuan et al. | |
| 2007/0037058 | A1 * | 2/2007 | Visco | H01M 12/065 429/246 |
| 2007/0066902 | A1 * | 3/2007 | Wilser | A61B 8/445 600/459 |
| 2008/0183166 | A1 * | 7/2008 | Miller | A61N 7/02 606/41 |
| 2008/0294154 | A1 * | 11/2008 | Ibrahim | A61B 18/1492 606/13 |
| 2008/0297135 | A1 * | 12/2008 | Lin | G01N 27/4145 324/71.1 |
| 2009/0292199 | A1 * | 11/2009 | Bielewicz | A61B 8/445 600/424 |
| 2011/0089903 | A1 * | 4/2011 | Heikkinen | H01M 10/425 320/126 |
| 2011/0112445 | A1 | 5/2011 | Naldoni | |
| 2011/0303013 | A1 * | 12/2011 | Kass | G01N 29/28 73/632 |
| 2012/0095343 | A1 * | 4/2012 | Smith | G01S 15/8913 600/447 |
| 2012/0095347 | A1 | 4/2012 | Adam et al. | |
| 2012/0103097 | A1 * | 5/2012 | Lopez Jauregui | G01N 29/2412 73/643 |
| 2013/0144166 | A1 * | 6/2013 | Specht | A61B 8/4444 600/441 |
| 2013/0178764 | A1 * | 7/2013 | Eckhouse | A61N 5/025 601/2 |
| 2014/0259604 | A1 * | 9/2014 | Romano | A61B 8/4422 29/426.2 |
| 2014/0268529 | A1 * | 9/2014 | Katsumoto | A61M 1/28 361/679.4 |
| 2014/0360274 | A1 * | 12/2014 | Cho | A61B 8/4427 73/644 |
| 2017/0112476 | A1 * | 4/2017 | Belevich | A61B 8/4494 |
| 2017/0119348 | A1 | 5/2017 | Degertekin et al. | |
| 2017/0303896 | A1 | 10/2017 | Bar-Tal et al. | |
| 2018/0249911 | A1 * | 9/2018 | Hosoda | G01N 21/4785 |

* cited by examiner

ULTRASOUND PROBE

CROSS-REFERENCE TO RELATED APPLICATION

This application is based on and claims priority under 35 U.S.C. § 119 to Korean Patent Application No. 10-2018-0011929, filed on Jan. 31, 2018, in the Korean Intellectual Property Office, the disclosure of which is incorporated by reference herein in its entirety.

BACKGROUND

1. Field

The present disclosure relates to an ultrasound probe, and more particularly, to an ultrasound probe with ease of use.

2. Description of the Related Art

An ultrasonic imaging apparatus irradiates ultrasound signals toward a target area of an object at the surface of the object, and receives ultrasound signals (echo ultrasound signals) reflected from the object so as to noninvasively acquire section images about soft tissue of the object or images about blood vessels of the object based on information of the echo ultrasound signals, thereby providing information about the object.

The ultrasonic imaging apparatus has advantages that it is a compact, low-priced apparatus and it can display images in real time, compared to other medical imaging apparatuses, such as an X-ray diagnostic apparatus, an X-ray Computerized Tomography (CT) scanner, a Magnetic Resonance Image (MRI) apparatus, and a nuclear medical diagnostic apparatus. Also, the ultrasonic imaging apparatus has high safety since there is no risk for patients to be exposed to radiation such as X-rays. For the advantages, the ultrasonic imaging apparatus is widely used to diagnose the heart, abdomen, urinary organs, uterus, etc.

The ultrasound imaging apparatus includes an ultrasound probe for sending and receiving ultrasonic waves. The ultrasound probe sends ultrasonic waves to an object through a transducer, and receives echo ultrasonic waves reflected from the object.

Meanwhile, an ultrasound probe for diagnosing animals has a larger size and a heavier weight than a general ultrasound probe, and accordingly, the ultrasound probe for diagnosing animals is disadvantageous in view of ease of use, such as portability and storage.

SUMMARY

Therefore, it is an aspect of the present disclosure to provide an ultrasound probe with ease of use, such as portability and storage.

It is another aspect of the present disclosure to provide an ultrasound probe capable of improving image quality.

Additional aspects of the disclosure will be set forth in part in the description which follows and, in part, will be obvious from the description, or may be learned by practice of the disclosure.

In accordance with an aspect of the present disclosure, an ultrasound probe includes a first assembly having a first case, a second assembly coupled with the first assembly, having a second case, and configured to be rotatable between a first position of being unfolded with respect to the first assembly and a second position of being folded on the first assembly, a first acoustic module disposed in the inside of the first case, a second acoustic module disposed in the inside of the second case, and a first space reducing portion disposed in at least one of a portion of the first case toward the second assembly and a portion of the second case toward the first assembly, and configured to reduce a space between the first acoustic module and the second acoustic module when the second assembly is at the first position.

When the first space reducing portion is disposed in the first case, the first space reducing portion may have a thinner thickness than the other portion of the first case, and when the first space reducing portion is disposed in the second case, the first space reducing portion may have a thinner thickness than the other portion of the second case.

When the first space reducing portion is disposed in the first case, the first space reducing portion may expose at least one portion of the first acoustic module to the outside of the first case, and when the first space reducing portion is disposed in the second case, the first space reducing portion may expose at least one portion of the second acoustic module to the outside of the second case.

When the second assembly is at the first position, a portion of the first acoustic module exposed to the outside of the first case through the first space reducing portion may contact a portion of the second acoustic module exposed to the outside of the second case through the first space reducing portion.

The ultrasound probe may further include a second space reducing portion disposed in at least one of a portion of the first case toward the second assembly and a portion of the second case toward the first assembly, and configured to reduce a space between the first acoustic module and the second acoustic module when the second assembly is at the second position.

When the second space reducing portion is disposed in the first case, the second space reducing portion may have a thinner thickness than the other portion of the first case, and when the second space reducing portion is disposed in the second case, the second space reducing portion may have a thinner thickness than the other portion of the second case.

The second space reducing portion may expose at least one of the first acoustic module and the second acoustic module to the outside.

The ultrasound probe may further include a hinge unit rotatably connecting the first assembly to the second assembly, and a connection member electrically connecting the first assembly to the second assembly, and passing the hinge unit.

The connection member may pass a rotation shaft of the hinge unit.

The connection member may include at least one of a Flexible Printed Circuit Board (FPCB) and a cable.

The ultrasound probe may further include a hinge unit rotatably connecting the first assembly to the second assembly, a connection member accommodating portion connecting the first assembly to the second assembly, and made of a flexible material, and a connection member electrically connecting the first assembly to the second assembly, and disposed in the inside of the connection member accommodating portion.

The ultrasound probe may further include a controller configured to produce an image based on information received from at least one of the first acoustic module and the second acoustic module, wherein the first acoustic module may include a plurality of first elements, the second acoustic module may include a plurality of second elements, when the second assembly is at the first position, the controller may produce an image of a space between the first assembly and the second assembly, based on a mean value of at least one first element adjacent to the second assembly among the plurality of first elements and at least one second element adjacent to the first assembly among the plurality of second elements.

In accordance with an aspect of the present disclosure, an ultrasound probe include a first assembly having a first case, a second assembly coupled with the first assembly, having a second case, and configured to be rotatable between a first position of being unfolded with respect to the first assembly and a second position of being folded on the first assembly, a first acoustic module disposed in the inside of the first case, a second acoustic module disposed in the inside of the second case, and a first space reducing portion disposed in at least one of the first case and the second case, and configured to reduce a space between the first acoustic module and the second acoustic module when the second assembly is at the first position, wherein when the first space reducing portion is disposed in the first case, the first space reducing portion has a thinner thickness than the other portion of the first case, and when the first space reducing portion is disposed in the second case, the first space reducing portion has a thinner thickness than the other portion of the second case.

The ultrasound probe may further include a second space reducing portion disposed in at least one of the first case and the second case, and configured to reduce a space between the first acoustic module and the second acoustic module when the second assembly is at the second position.

When the second space reducing portion is disposed in the first case, the second space reducing portion may have a thinner thickness than the other portion of the first case, and when the second space reducing portion is disposed in the second case, the second space reducing portion may have a thinner thickness than the other portion of the second case.

The second space reducing portion may expose at least one of the first acoustic module and the second acoustic module to the outside.

The ultrasound probe may further include a controller configured to produce an image based on information received from at least one of the first acoustic module and the second acoustic module, wherein the first acoustic module may include a plurality of first elements, the second acoustic module may include a plurality of second elements, and when the second assembly is at the first position, the controller may produce an image of a space between the first assembly and the second assembly, based on a mean value of at least one first element adjacent to the second assembly among the plurality of first elements and at least one second element adjacent to the first assembly among the plurality of second elements.

In accordance with an aspect of the present disclosure, an ultrasound probe includes a first assembly having a first case, a second assembly coupled with the first assembly, having a second case, and configured to be rotatable between a first position of being unfolded with respect to the first assembly and a second position of being folded on the first assembly, a first acoustic module disposed in the inside of the first case, a second acoustic module disposed in the inside of the second case, and a first space reducing portion disposed in at least one of the first case and the second case, and configured to reduce a space between the first acoustic module and the second acoustic module when the second assembly is at the first position, wherein when the first space reducing portion is disposed in the first case, the first space reducing portion exposes at least one portion of the first acoustic module to the outside of the first case, and when the first space reducing portion is disposed in the second case, the first space reducing portion exposes at least one portion of the second acoustic module to the outside of the second case.

When the second assembly is at the first position, a portion of the first acoustic module exposed to the outside of the first case through the first space reducing portion may contact a portion of the second acoustic module exposed to the outside of the second case through the first space reducing portion.

The ultrasound probe may further include a second space reducing portion disposed in at least one of a portion of the first case toward the second assembly and a portion of the second case toward the first assembly, and configured to reduce a space between the first acoustic module and the second acoustic module when the second assembly is at the second position.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
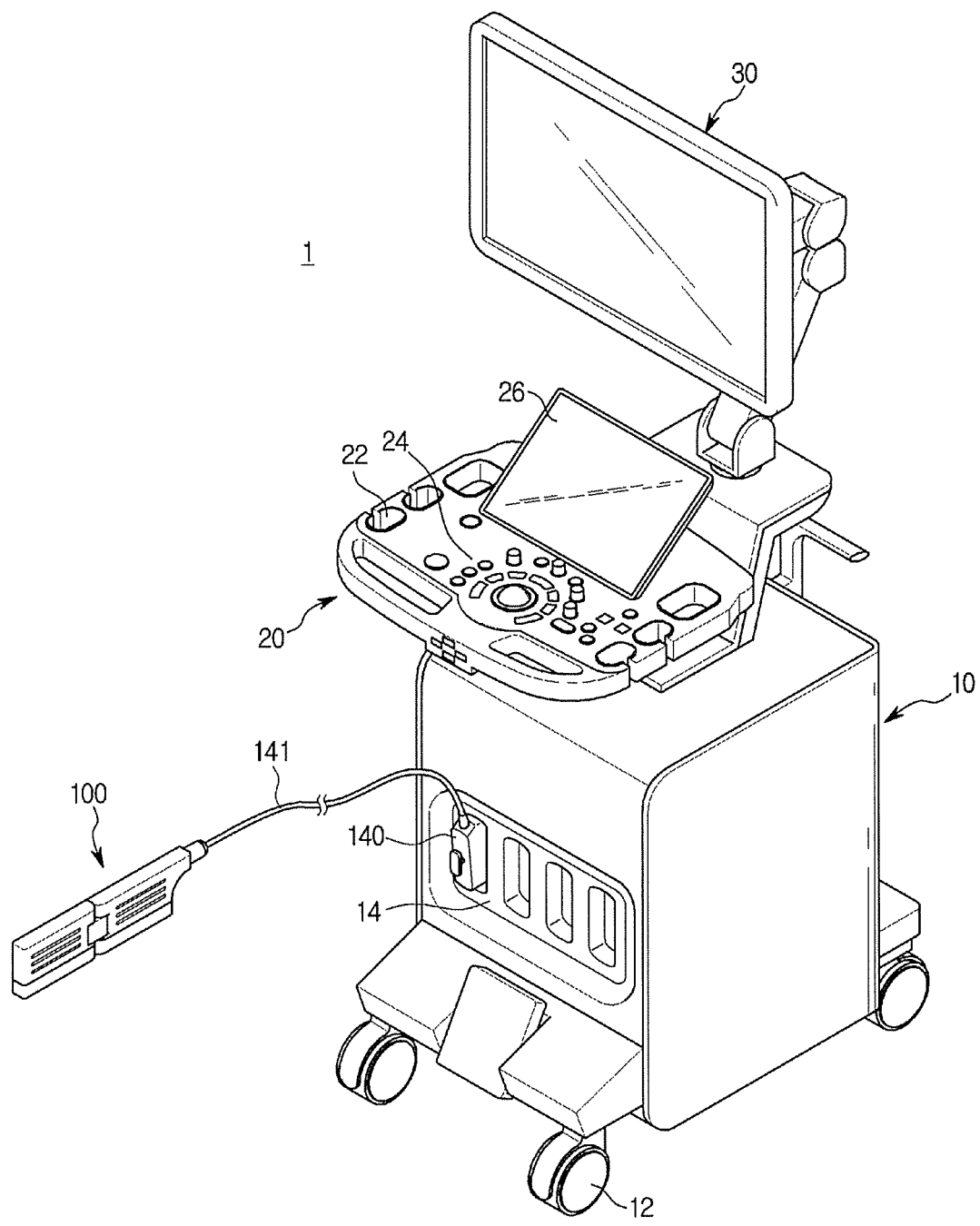
FIG. 1 shows medical equipment in which an ultrasound probe according to an embodiment of the present disclosure can be used.

Configurations illustrated in the embodiments and the drawings described in the present specification are only the preferred embodiments of the present disclosure, and thus it is to be understood that various modified examples, which may replace the embodiments and the drawings described in the present specification, are possible when filing the present application.

Also, like reference numerals or symbols denoted in the drawings of the present specification represent members or components that perform the substantially same functions.

The terms used in the present specification are used to describe the embodiments of the present disclosure. Accordingly, it should be apparent to those skilled in the art that the following description of the exemplary embodiments of the present disclosure is provided for illustration purpose only and not for the purpose of limiting the disclosure. It is to be understood that the singular forms "a," "an," and "the" include plural referents unless the context clearly dictates otherwise. It will be understood that when the terms "includes," "comprises," "including," and/or "comprising," when used in this specification, specify the presence of stated features, figures, steps, components, or combination thereof, but do not preclude the presence or addition of one or more other features, figures, steps, components, members, or combinations thereof.

Also, it will be understood that, although the terms first, second, etc. may be used herein to describe various components, these components should not be limited by these terms. These terms are only used to distinguish one component from another. For example, a first component could be termed a second component, and, similarly, a second component could be termed a first component, without departing from the scope of the present disclosure. As used herein, the term "and/or" includes any and all combinations of one or more of associated listed items.

Meanwhile, in the following description, the terms "rear", "upper", "lower", etc. are defined based on the drawings, and the shapes and positions of the components are not limited by the terms.

Hereinafter, the embodiments of the present disclosure will be described in detail with reference to the accompanying drawings.

FIG. 1 shows medical equipment in which an ultrasound probe according to an embodiment of the present disclosure can be used.

Referring to FIG. 1, medical equipment 1 according to an embodiment of the present disclosure may include a main body 10, and an ultrasound probe 100 for sending an ultrasound signal to an object to be diagnosed and receiving a signal reflected from the object. The ultrasound probe 100 may be connected to the main body 10 by a cable 141.

The ultrasound probe 100 may be put in a holder 22 to be fixed at the main body 10. When a user does not use the medical equipment 1, the user may put the ultrasound probe 100 in the holder 22 to keep the ultrasound probe 100. In FIG. 1, the holder 22 for putting the ultrasound probe 100 therein is provided in a control panel 20. However, the holder 22 may be provided in the main body 10 according to user convenience. Also, two holders 22 may be provided in both the main body 10 and the control panel 20, respectively.

In the main body 10, a moving apparatus 12 for moving the medical equipment 1 may be provided. The moving apparatus 12 may be a plurality of casters attached on a bottom of the main body 10. The casters may be aligned to move the main body 10 in a predetermined direction, arranged to move the main body 10 in an arbitrary direction, or locked to stop the main body 10 at a predetermined position.

The ultrasound probe 100 may include a plurality of acoustic modules 150a and 150b (also, referred to as a first acoustic module 150a and a second acoustic module 150b) installed in a case 110. Each of the acoustic modules 150a and 150b may include a transducer module for irradiating ultrasonic waves toward an object, receiving echo ultrasonic waves reflected from the object, and converting electrical signals into ultrasonic waves and ultrasonic waves into electrical signals. The ultrasound probe 100 may include a male connector 140 physically coupled with a female connector 14 of the main body 10 to send/receive signals to/from the main body 10, and the cable 141 connecting the male connector 140 to the acoustic modules 150a and 150b.

The object may be a human's or animal's body part, or tissue in a body part, such as vessels, bonds, and muscles. However, the object is not limited to the above-mentioned body part or tissue, and may be anything whose inner structure can be imaged by the medical equipment 1, that is, an ultrasonic imaging apparatus.

The echo ultrasonic waves may be ultrasonic waves reflected from the object to which ultrasonic waves have been irradiated, and may have various frequency bands or energy levels to produce various ultrasound images according to diagnosis modes.

The acoustic modules 150a and 150b may generate ultrasonic waves according to alternating-current (AC) power applied thereto. More specifically, the acoustic modules 150a and 150b may receive AC power from an external power supply or from an internal power storage unit, for example, a battery. Vibrators of the acoustic modules 150a and 150b may vibrate according to the AC power to generate ultrasonic waves.

One end of the cable 141 may be connected to the transducer module 110, and the other end of the cable 141 may be connected to the male connector 140, so as to connect the acoustic modules 150a and 150b to the male connector 140. The male connector 140 may be physically coupled with the female connector 14 of the main body 10. The male connector 140 may transfer electrical signals generated by the acoustic modules 150a and 150b to the female connector 14, or may receive control signals generated by the main body 10 from the female connector 14.

In FIG. 1, the male connector 140 and the cable 141 are exposed to the outside. However, the male connector 140 and the cable 141 may be installed in a housing forming the main body 10.

Meanwhile, on the main body 10 of the medical equipment 1, a display 30 and a control panel 20 may be mounted. On the control panel 20, an input device 24 may be provided to enable a user to control the medical equipment 1. The input device 24 may receive various control commands, as well as setting information about the ultrasound probe 100, from the user.

According to an embodiment, the setting information about the ultrasound probe 100 may include gain information, zoom information, focus information, Time Gain Compensation (TGC) information, depth information, frequency information, power information, frame average information, dynamic range information, etc. However, the setting information about the ultrasound probe 100 is not limited to the above-mentioned information, and may include various information that can be set in order to photograph ultrasound images.

The information may be transferred to the ultrasound probe 100 through the cable 141, and the ultrasound probe 100 may be set according to the received information. Also, the main body 10 may receive various control commands, such as a command for transmitting an ultrasound signal, through the input device 24, from the user, and transfer the various control commands to the ultrasound probe 100.

Meanwhile, the input device 24 may be implemented as a keyboard, a foot switch, or a foot pedal. For example, the keyboard may be hardwarily implemented. The keyboard may include at least one of a switch, a key, a joystick, and a trackball. According to another example, the keyboard may be softwarily implemented, like a graphic user interface. In this case, the keyboard may be displayed through the display 30. The foot switch or the foot pedal may be disposed below the main body 10, and the user may control operations of the medical equipment 1 using the foot switch or the foot pedal.

The display 30 may be a Cathode Ray Tube (CRT) display, a Liquid Crystal Display (LCD), a Light Emitting Diodes (LED) display, a Plasma Display Panel (PDP) display, or an Organic Light Emitting Diode (OLED) display, although not limited to these.

The display 30 may display an ultrasound image about a target part of an object. The ultrasound image displayed on the display 30 may be a 2D ultrasound image or a 3D ultrasound image. The display 300 may display various ultrasound images according to operation modes of the medical equipment 1. Also, the display 30 may display information related to an operation state of the ultrasound probe 100, as well as a menu or guidance needed for ultrasonic diagnosis.

According to an embodiment, the ultrasound image may include an Amplitude-mode (A-mode) image, a Brightness-mode (B-mode) image, a Motion-mode (M-mode) image, a Color-mode (C-mode) image, and a Doppler-mode (D-mode) image.

The A-mode image means an ultrasound image representing the amplitude of an ultrasound signal corresponding to an echo ultrasound signal, the B-mode image means an ultrasound image representing the amplitude of an ultrasound signal corresponding to an echo ultrasound signal as brightness, and the M-mode image means an ultrasound image representing the motion of an object ob according to time at a specific location. The D-mode image means an ultrasound image representing a moving object ob in the form of a waveform using the Doppler effect, and the C-mode image means an ultrasound image representing a moving object ob in the form of a color spectrum.

Meanwhile, a secondary display 26 may be mounted on the control panel 20. The secondary display 26 may provide a menu for optimizing ultrasound images, or related information such as secondary images, or may provide the user with a graphic interface.

Also, if the secondary display 26 is implemented as a touch screen, the display 30 may function as the input device 24. That is, the main body 10 may receive various commands from the user, through at least one of the display 30 and the input device 24. Also, the main body 10 may include a voice recognition sensor for receiving voice commands from the user, although not shown in the drawings.

Figure 2:
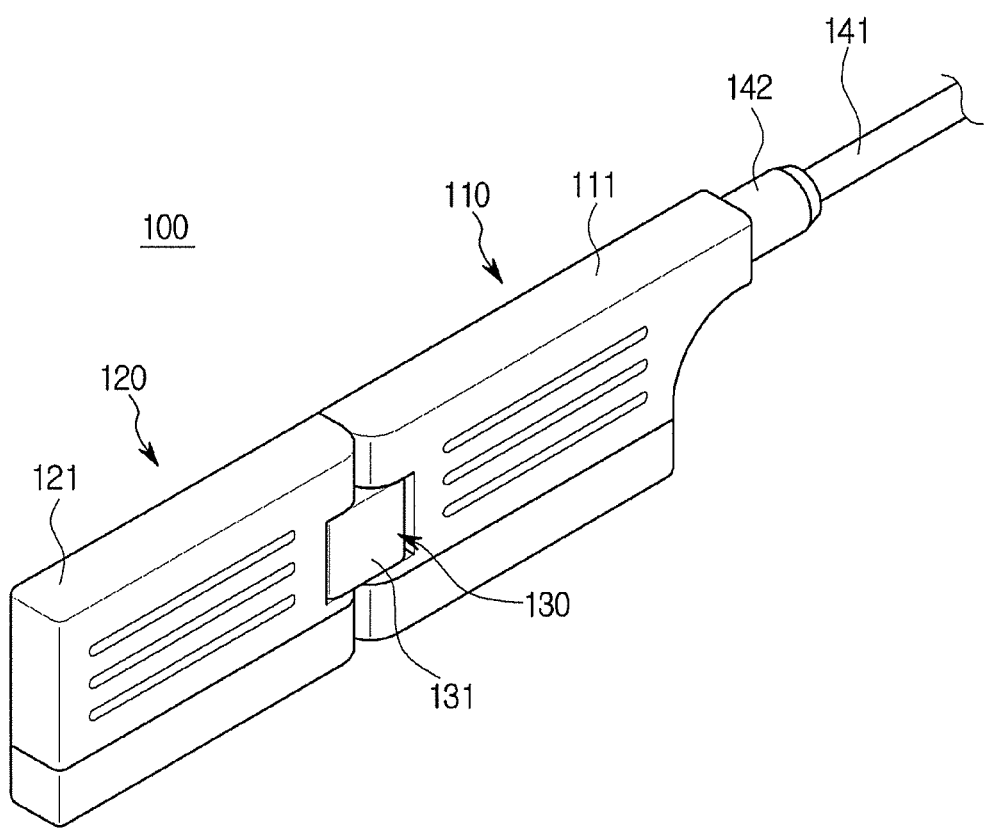
FIG. 2 shows the ultrasound probe shown in FIG. 1 when the ultrasound probe is unfolded.
Figure 3:
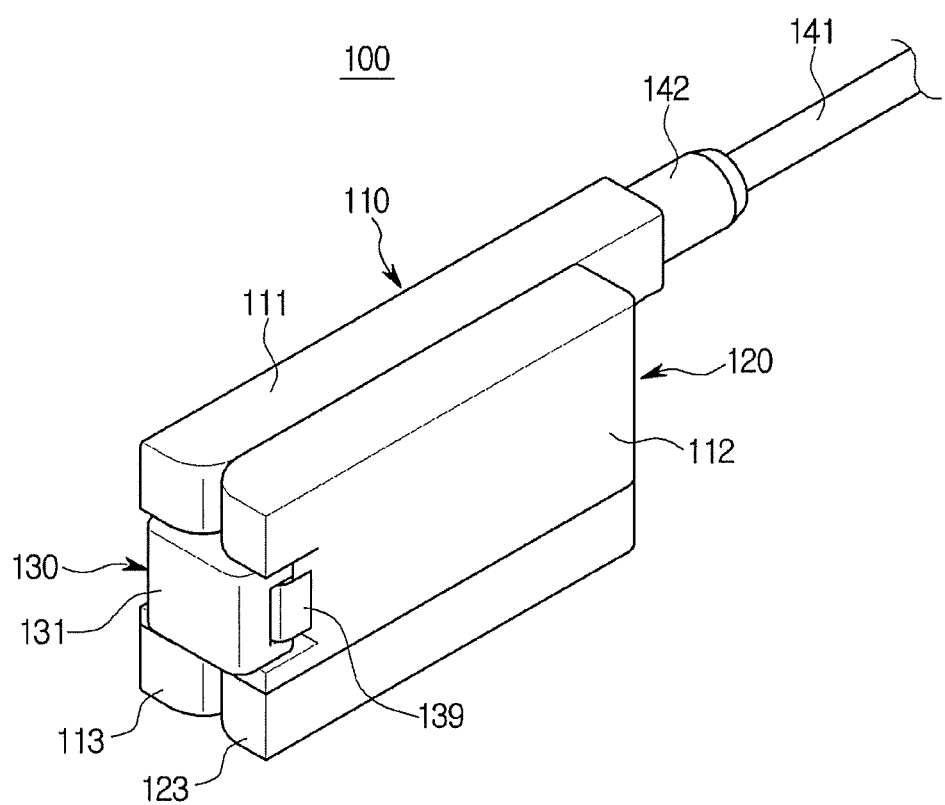
FIG. 3 shows the ultrasound probe shown in FIG. 1 when the ultrasound probe is folded.
Figure 4:
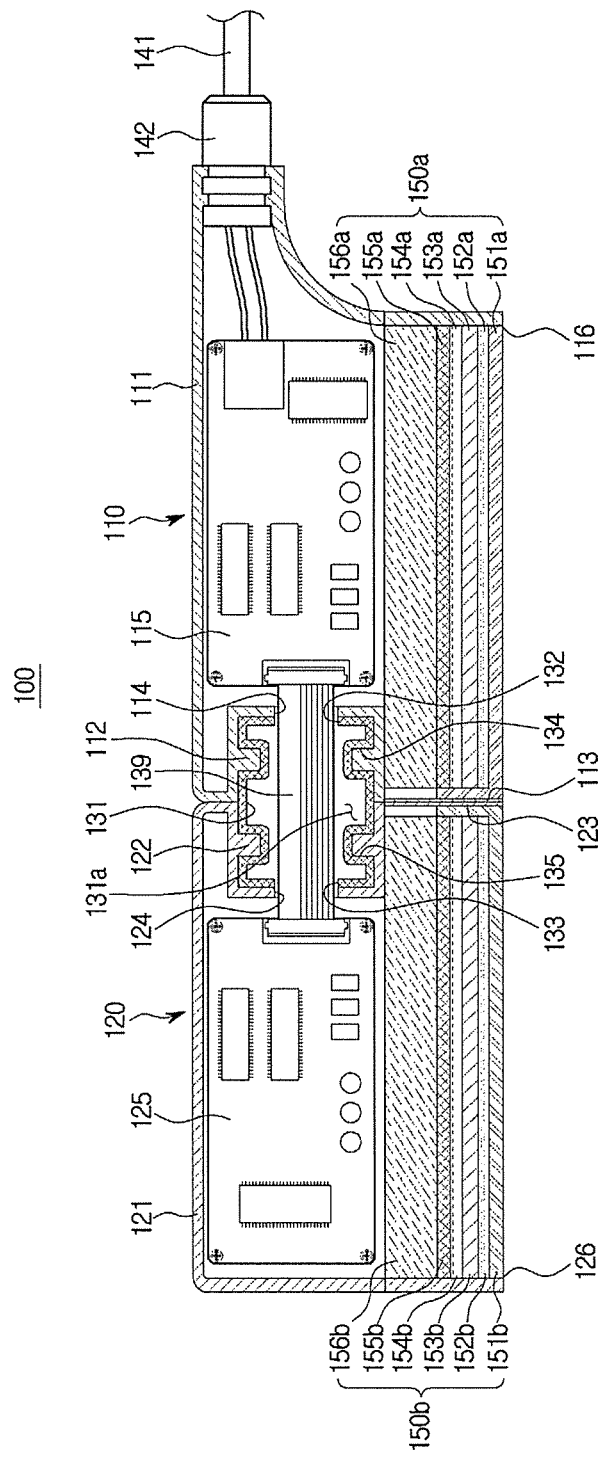
FIG. 4 shows the inside of the ultrasound probe shown in FIG. 1.
Figure 5:
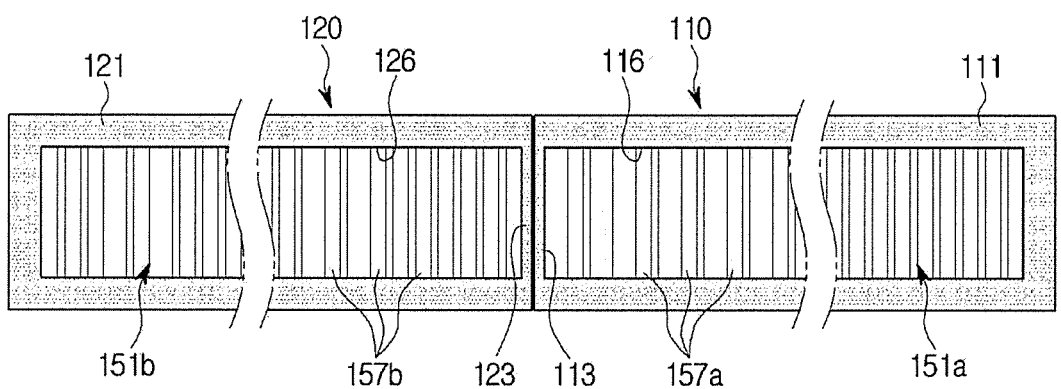
FIG. 5 shows a bottom of the ultrasound probe shown in FIG. 2.

FIG. 2 shows the ultrasound probe shown in FIG. 1 when the ultrasound probe is unfolded. FIG. 3 shows the ultrasound probe shown in FIG. 1 when the ultrasound probe is folded. FIG. 4 shows the inside of the ultrasound probe shown in FIG. 1. FIG. 5 shows a bottom of the ultrasound probe shown in FIG. 2.

Referring to FIGS. 2, 3, and 4, the ultrasound probe 100 may include a first assembly 110, a second assembly 120, and a hinge unit 130 rotatably coupling the second assembly 120 with the first assembly 110.

The first assembly 110 may include a first case 111 forming an outer appearance of the first assembly 110. In the inside of the first case 111, a first electronic component 115 and/or the first acoustic module 150a may be installed. The first case 111 may include a first lens opening 116 for exposing a first lens 151a of the first acoustic module 150a to the outside. The first lens opening 116 may be formed in a side of the ultrasound probe 100 facing an object when the object is inspected with the ultrasound probe 100.

The first assembly 110 may include a cable connecting portion 142 connected to the cable 141. The cable connecting portion 142 may be formed at one end of the first case 111. The cable 141 guided into the inside of the first assembly 110 via the cable connecting portion 142 may be electrically connected to the first electronic component 115 installed in the inside of the first assembly 110.

The first electronic component 115 may be installed in the inside of the first case 111 to drive the first assembly 110. The first electronic component 115 may drive the first acoustic module 150a. The first electronic component 115 may be electrically connected to a second electronic component 125 of the second assembly 120 by a connecting member 139.

The first case 111 may include a first fixing protrusion 112 with which the hinge unit 130 is rotatably coupled. A plurality of first fixing protrusions 112 may be provided to face each other. The first fixing protrusion 112 may be rotatably inserted into a first fixing groove 134 of the hinge unit 130.

The first case 111 may include a first connecting opening 114 through which the connecting member 139 electrically connecting the first assembly 110 to the second assembly 120 passes. The first connecting opening 114 may be formed to correspond to a size of the connecting member 139. The first connecting opening 114 may be formed in a portion of the first case 111 with which the hinge unit 130 is coupled.

The second assembly 120 may include a second case 121 forming an outer appearance of the second assembly 120. In the inside of the second case 121, the second electric component 125 and/or the second acoustic module 150b may be installed. The second case 121 may include a second lens opening 126 for exposing a second lens 151b of the second acoustic module 150b to the outside. The second lens opening 126 may be formed in the side of the ultrasound probe 100 facing an object when the object is inspected with the ultrasound probe 100.

The second electronic component 125 may be installed in the inside of the second case 121 to drive the second assembly 120. The second electronic component 125 may drive the second acoustic module 150b. The first electronic component 125 may be electrically connected to the first electronic component 115 of the first assembly 110 by the connecting member 139.

The second case 121 may include a second fixing protrusion 122 with which the hinge unit 130 is rotatably coupled. A plurality of second fixing protrusions 122 may be provided to face each other. The second fixing protrusion 122 may be rotatably inserted into the second fixing groove 135 of the hinge unit 130.

The second case 121 may include a second connecting opening 124 through which the connecting member 139 electrically connecting the second assembly 120 to the first assembly 110 passes. The second connecting opening 124 may be formed to correspond to a size of the connecting member 139. The second connecting opening 124 may be formed in a portion of the second case 121 with which the hinge unit 130 is coupled.

The hinge unit 130 may electrically connect the second assembly 120 to the first assembly 110. The hinge unit 130 may include a hinge body 131, a first opening 132, a second opening 133, the first fixing groove 134, and the second fixing groove 135.

The hinge body 131 may be rotatably connected to the first assembly 110 at one end, and rotatably connected to the second assembly 120 at the other end. The hinge body 131 may include a space 131a in which the connecting member 139 is installed.

The first opening 132 may pass the connecting member 139 through. The first opening 132 may be formed at one end of the hinge body 131 toward the first assembly 110.

The second opening 133 may pass the connecting member 139 through. The second opening 133 may be formed at the other end of the hinge body 131 toward the second assembly 120.

The first fixing protrusion 112 of the first assembly 110 may be rotatably inserted into the first fixing groove 134. A size and shape of the first fixing groove 134 may correspond to those of the first fixing protrusion 112. The number of the first fixing groove 134 may also correspond to that of the first fixing protrusion 112.

The second fixing protrusion 122 of the second assembly 120 may be rotatably inserted into the second fixing groove 135. A size and shape of the second fixing groove 135 may correspond to those of the second fixing protrusion 122. The number of the second fixing groove 135 may also correspond to that of the second fixing protrusion 122.

The connecting member 139 may electrically connect the second assembly 120 to the first assembly 110. The connecting member 139 may pass the hinge unit 130. The connecting member 139 may be connected to the first electric component 115 at one end, pass through the first connecting opening 114, the first opening 132, the second opening 133, and the second connecting opening 124, and then be connected to the second electric component 125 at the other end. The connecting member 139 may be made of a flexible material. The connecting member 139 may be a Flexible Printed Circuit Board (FPCB). The connecting member 139 may be a cable.

The first acoustic module 150a may be installed in the inside of the first case 111 of the first assembly 110. The first acoustic module 150a may include the first lens 151a, a first foreign material blocking layer 152a, a first matching layer 153a, a first piezoelectric layer 154a, a first sound-absorption layer 155a, and a first sound-reflection layer 156a.

The first lens 151a may be disposed at an outermost portion of the first acoustic module 150a. The first lens 151a may focus ultrasonic waves generated by the first piezoelectric layer 154a. The first lens 151a may be made of a material, such as silicon and rubber, having acoustic impedance that is similar to acoustic impedance of an object. The first lens 151a may be a convex type whose center portion has a convex curved surface, or a linear type having a flat surface.

The first foreign material blocking layer 152a may block foreign materials from entering the inside of the first case 111. The first foreign material blocking layer 152a may be made of a material that passes ultrasonic waves through.

The first matching layer 153a may reduce a difference in acoustic impedance between the first piezoelectric layer 154a and an object to match acoustic impedance of the first piezoelectric layer 154a with acoustic impedance of the object so that ultrasonic waves generated by the first piezoelectric layer 154a can be efficiently transferred to the object.

For this, the first matching layer 153a may have acoustic impedance corresponding to a median value of acoustic impedance of the first piezoelectric layer 154a and acoustic impedance of the object. More specifically, the first matching layer 153a may have a median value of acoustic impedance of the first piezoelectric layer 154a and acoustic impedance of the object.

Also, the first matching layer 153a may be a plurality of layers so that acoustic impedance can change gradually toward the object from the first piezoelectric layer 154a. The plurality of matching layers may be made of different materials. The first matching layer 153a may be made of glass or a resin.

An effect in which a voltage is generated when mechanical pressure is applied to a predetermined material, and an effect in which mechanical deformation occurs when a voltage is applied are called a piezoelectric effect and a converse piezoelectric effect, respectively. The first piezoelectric layer 154a may contain a piezoelectric material having the piezoelectric effect and the converse piezoelectric effect. That is, the piezoelectric material is a material of converting electricity energy into mechanical vibration energy and mechanical vibration energy into electricity energy.

That is, the first piezoelectric layer 154a may be a piezoelectric layer, and the piezoelectric layer may vibrate to convert an electrical signal into a sound signal and a sound signal into an electrical signal. Also, an electrode for receiving electrical signals may be formed above or below the first piezoelectric layer 154a, although not shown in the drawings.

More specifically, the piezoelectric material forming the first piezoelectric layer 154a may be ceramic of lead zirconate titanate (PZT), PZMT single crystal made of a solid solution of lead magnesium niobate and lead titanate, or PZNT single crystal made of a solid solution of lead zinc niobate and lead titanate.

That is, the first piezoelectric layer 154a according to an embodiment of the present disclosure may be made of a piezoelectric material that converts, when an electrical signal is applied, the electrical signal into mechanical vibrations to generate ultrasonic waves.

The first piezoelectric layer 154a may be a piezoelectric ultrasonic transducer using the piezoelectric effect of a piezoelectric material. However, the first piezoelectric layer 154a may be a magnetostrictive ultrasonic transducer using the magnetostrictive effect of a magnetic material, or a capacitive micromachined ultrasonic transducer (cMUT) that transmits and receives ultrasonic waves using vibration of several hundreds or thousands of micromachined thin films.

The first sound-absorption layer 155a may function to prevent an ultrasound signal from being transferred in a rear direction of the ultrasound probe 100 and to absorb or reflect an ultrasound signal transferred in the rear direction of the ultrasound probe 100, thereby preventing image distortion. Also, the first sound-absorption layer 155a may focus an ultrasound signal to be sent at a predetermined location in an elevation direction of the ultrasound probe 100.

More specifically, the first sound-absorption layer 155a may suppress free vibrations of the first piezoelectric layer 154a to reduce a pulse width of ultrasonic waves, and may prevent ultrasonic waves from being propagated unnecessarily in the rear direction of the first piezoelectric layer 154a, thereby preventing distortion of ultrasound images. The first sound-absorption layer 155a may be made of a material including rubber containing an epoxy resin, tungsten power, etc.

The first sound-reflection layer 156a may totally reflect ultrasonic waves passed through the first sound-absorption layer 155a. Thereby, the ultrasound probe 100 may have a wide bandwidth and high sensitivity.

The first sound-reflection layer 156a may be made of a material having very high acoustic impedance in order to totally reflect ultrasonic waves. For example, the first sound-reflection layer 156a may contain at least one material among tungsten carbide and a graphite compound.

The first sound-reflection layer 156a may have higher acoustic impedance than the first piezoelectric layer 154a. The first sound-reflection layer 156a may be made of a material having electrical conductivity. Also, a thickness of the first sound-reflection layer 156a may be ½, ¼, ⅛, or ¹⁄₁₆ of the wavelength of the piezoelectric material constituting the first piezoelectric layer 154a. That is, if the wavelength of the piezoelectric material constituting the first piezoelectric layer 154a is $\lambda$, the thickness of the first sound-reflection layer 156a may be $½\lambda$, $¼\lambda$, $⅛\lambda$, or $¹⁄_{16}\lambda$.

The second acoustic module 150b may be installed in the inside of the second case 121 of the second assembly 120. The second acoustic module 150b may include the second lens 151b, a second foreign material blocking layer 152b, a second matching layer 153b, a second piezoelectric layer 154b, a second sound-absorption layer 155b, and a second sound-reflection layer 156b. The second lens 151b, the second foreign material blocking layer 152b, the second matching layer 153b, the second piezoelectric layer 154b, the second sound-absorption layer 155b, and the second sound-reflection layer 156b may be the same configuration as the first lens 151a, the first foreign material blocking layer 152a, the first matching layer 153a, the first piezoelectric layer 154a, the first sound-absorption layer 155a, and the first sound-reflection layer 156a, and accordingly, detailed descriptions thereof will be omitted.

According to the configuration, the second assembly 120 may be rotatable between a first position of being unfolded with respect to the first assembly 110 and a second position of being folded on the first assembly 110. Accordingly, a user can fold the ultrasound probe 100 to carry it, and also can unfold the ultrasound probe 100 to use it, resulting in ease of use.

Meanwhile, when the second assembly 120 is unfolded with respect to the first assembly 110, the first acoustic module 150a may be spaced from the second acoustic module 150b. More specifically, the first acoustic module 150a may be spaced by a distance corresponding to a sum of a thickness of the first case 111 and a thickness of the second case 121 from the second acoustic module 150b. However, if the first acoustic module 150a is spaced from the second acoustic module 150b, image quality may deteriorate. Particularly, the ultrasound probe 100 for diagnosing large animals includes a plurality of acoustic modules since it is difficult to manufacture an acoustic module that is larger than a specific size, and in this case, spaces between the plurality of acoustic modules may cause a deterioration in image quality.

Referring to FIGS. 2 to 5, the ultrasonic probe 100 may include a plurality of first space reducing portions 113 and 123 in order to prevent a deterioration in image quality due to the space between the first acoustic module 150a and the second acoustic module 150b.

The first space reducing portions 113 and 123 may include a 1a-th space reducing portion 113 formed in the first case 111 of the first assembly 110, and a 1b-th space reducing portion 123 formed in the second case 121 of the second assembly 120. The first space reducing portions 113 and 123 may have a thinner thickness than the other portion of the first case 111 and/or the second case 121.

The 1a-th space reducing portion 113 may be positioned on a surface of the first case 111 facing the second assembly 120 when the second assembly 120 is at the first position at which it is unfolded with respect to the first assembly 110. The 1a-th space reducing portion 113 may be disposed to correspond to one edge of the first acoustic module 150a. The 1a-th space reducing portion 113 may have a thinner thickness than the other portion of the first case 111.

The 1b-th space reducing portion 123 may be positioned on a surface of the second case 121 facing the first assembly 110 when the second assembly 120 is at the first position at which it is unfolded with respect to the first assembly 110. The 1b-th space reducing portion 123 may be disposed to correspond to one edge of the first acoustic module 150b. The 1b-th space reducing portion 123 may have a thinner thickness than the other portion of the second case 121.

In FIGS. 4 and 5, both the first case 111 and the second case 121 include the first space reducing portions 113 and 123, respectively. However, the first space reducing portions 113 and 123 may be provided on the first case 111 or the second case 121.

According to the configuration, the ultrasound probe 100 according to an embodiment of the present disclosure can reduce the space between the first acoustic module 150a and the second acoustic module 150b, thereby preventing a deterioration in image quality.

Figure 6:
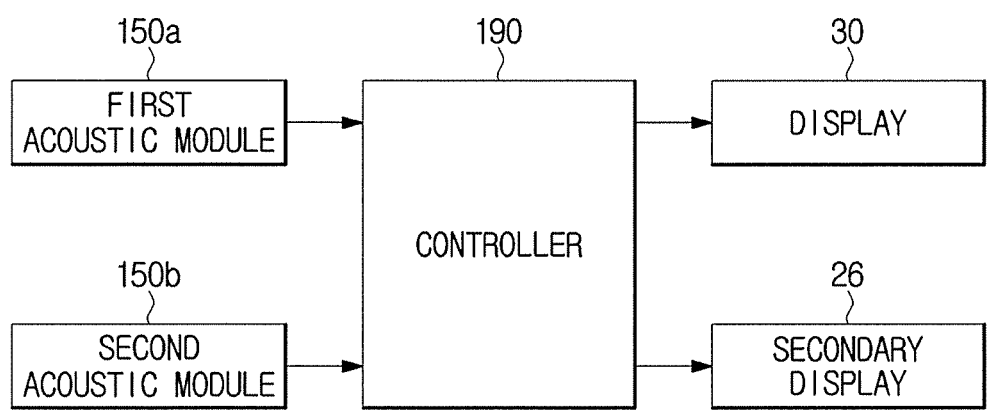
FIG. 6 is a control block diagram of the ultrasound probe shown in FIG. 1.

FIG. 6 is a control block diagram of the ultrasound probe shown in FIG. 1.

Referring to FIGS. 5 and 6, the first acoustic module 150a may include a plurality of first elements 157a, and the second acoustic module 150b may include a plurality of second elements 157b. The first elements 157a and the second elements 157b may convert ultrasonic signals into electrical signals and electrical signals into ultrasonic signals.

The ultrasound probe 100 according to an embodiment of the present disclosure may include a controller 190. The controller 190 may receive signals from the first acoustic module 150a and the second acoustic module 150b to produce an image. The controller 190 may produce an image, and transfer the image to the display 30 and/or the secondary display 26 to represent the image visually.

Meanwhile, when the second assembly 120 is at the first position at which it is unfolded with respect to the first assembly 110, the controller 190 may produce an image of the space between the first assembly 110 and the second assembly 120, based on a mean value of at least one first element 157a adjacent to the second assembly 120 among the plurality of first elements 157a and at least one second element 157b adjacent to the first assembly 110 among the plurality of second elements 157b. For example, when calculating the mean value, the controller 190 may receive signal information from three first elements 157a adjacent to the second assembly 120 and three second elements 157b adjacent to the first assembly 110.

According to the configuration, the ultrasound probe 100 according to an embodiment of the present disclosure may prevent a deterioration in image quality due to the space between the first acoustic module 150a and the second acoustic module 150b.

Figure 7:
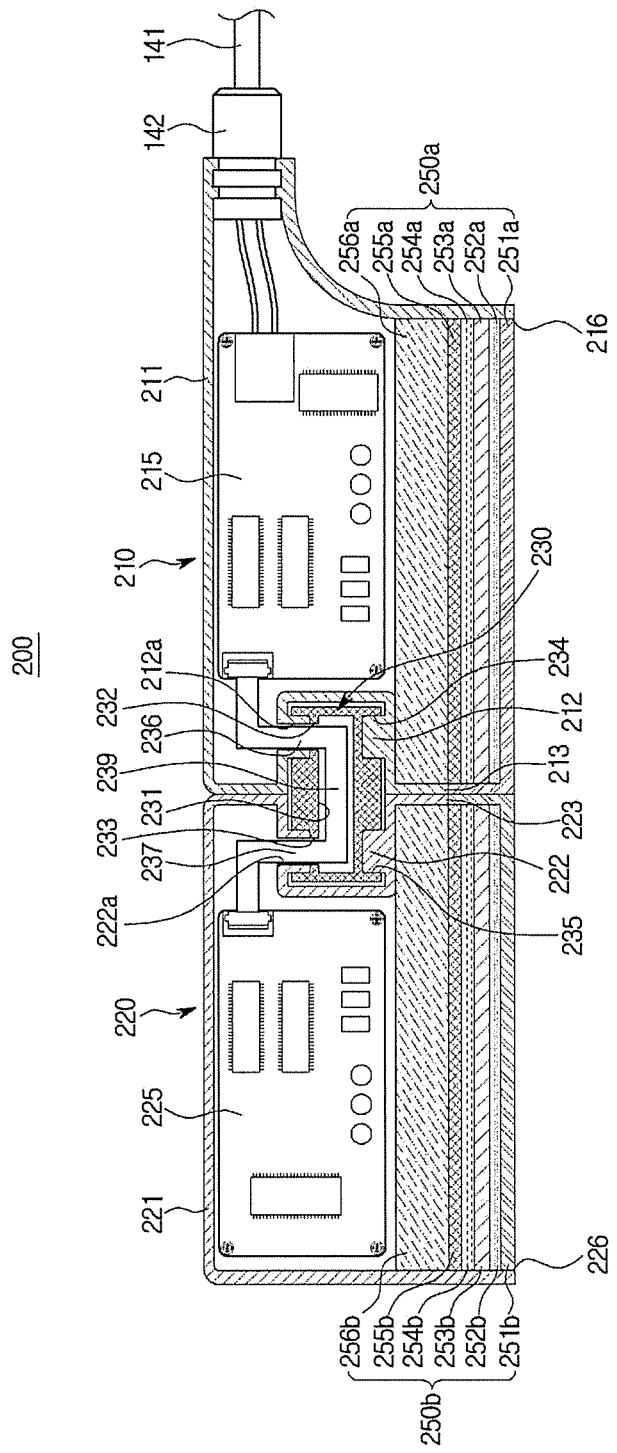
FIG. 7 shows the inside of an ultrasound probe according to another embodiment of the present disclosure.
Figure 8:
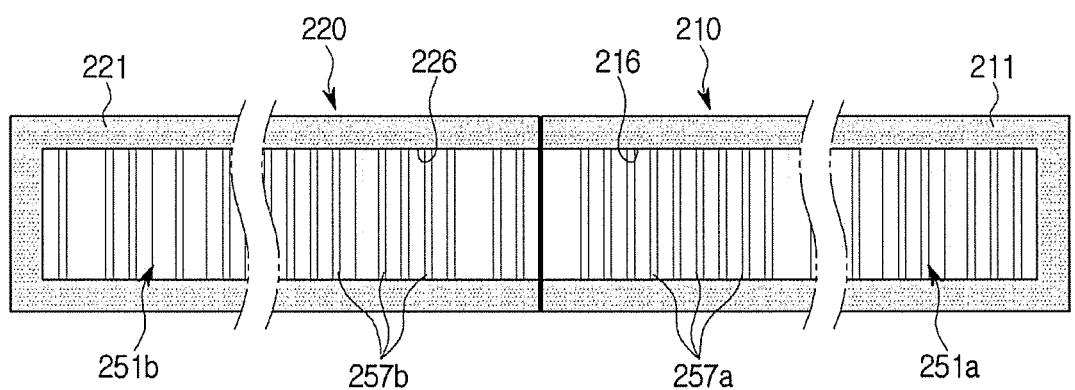
FIG. 8 shows a bottom of the ultrasound probe shown in FIG. 7.

FIG. 7 shows the inside of an ultrasound probe according to another embodiment of the present disclosure. FIG. 8 shows a bottom of the ultrasound probe shown in FIG. 7.

Referring to FIGS. 7 and 8, an ultrasound probe 200 according to another embodiment of the present disclosure will be described. In the following description, the same components as those described in the above-described embodiment will be assigned the same reference numerals, and detailed descriptions thereof will be omitted.

The ultrasound probe 200 may include a first assembly 210, a second assembly 220, and a hinge unit 230.

The first assembly 210 may include a first case 211, and in the inside of the first case 211, a first electronic component 215 and/or a first acoustic module 250a may be installed. The first case 211 may include a first lens opening 216 for exposing a first lens 251a to the outside.

The first acoustic module 250a may include a first lens 251a, a first foreign material blocking layer 252a, a first matching layer 253a, a first piezoelectric layer 254a, a first sound-absorption layer 255a, and a first sound-reflection layer 256a.

The second assembly 220 may include a second case 221. In the inside of the second case 221, a second electric component 225 and/or a second acoustic module 250b may be installed. The second case 221 may include a second lens opening 226 for exposing a second lens 251b to the outside.

The second acoustic module 250b may include the second lens 251b, a second foreign material blocking layer 252b, a second matching layer 253b, a second piezoelectric layer 254b, a second sound-absorption layer 255b, and a second sound-reflection layer 256b.

The hinge unit 230 may rotatably connect the second case 210 to the second case 220. The hinge unit 330 may include a hinge body 231.

The hinge body 231 may include a first fixing groove 234 into which a first fixing protrusion 212 is rotatably inserted. The hinge body 231 may include a second fixing groove 235 into which a second fixing protrusion 222 is rotatably inserted.

A connection member 239 according to an embodiment of the present disclosure may pass a rotation shaft of the hinge unit 230. That is, a first portion 236 of the connection member 239 may pass a first rotation shaft opening 212a of the first case 211 and a first rotation shaft opening 232 of the hinge body 231. Also, a second portion 237 of the connection member 239 may pass a second rotation shaft opening 222a of the second case 221 and a second rotation shaft opening 233 of the hinge body 231. Accordingly, the connection member 239 may electrically connect the first electronic component 215 of the first assembly 210 to the second electronic component 225 of the second assembly 220.

According to the configuration, the ultrasound probe 200 according to another embodiment of the present disclosure may prevent the connection member 239 from being exposed to the outside, when the second assembly 220 is at the second position at which it is folded on the first assembly 210.

The ultrasound probe 200 according to the other embodiment of the present disclosure may include a plurality of first space reducing portions 213 and 223 in order to prevent a deterioration in image quality due to the space between the first acoustic module 250a and the second acoustic module 250b. The plurality of first space reducing portions 213 and 223 may include a 1a-th space reducing portion 213 and a 1b-th space reducing portion 223.

The 1a-th space reducing portion 213 may expose at least one portion of the first acoustic module 250a to the outside of the first case 211, when it is disposed on the first case 211. That is, the 1a-th space reducing portion 213 may be formed in the shape of an opening in a side of the first case 211 facing the second assembly 220. The 1a-th space reducing portion 213 may extend less in a direction toward an object than the other side of the first case 211 that is opposite to the side of the first case 211 in which the 1a-th space reducing portion 213 is formed. Accordingly, the first lens 251a may be exposed to the outside.

The 1b-th space reducing portion 223 may expose at least one portion of the second acoustic module 250b to the outside of the second case 221, when it is disposed on the second case 221. That is, the 1b-th space reducing portion 223 may be formed in the shape of an opening at a side of the second case 221 facing the first assembly 210. The 1b-th space reducing portion 223 may be formed in the shape of an opening in a side of the second case 221 facing the second assembly 210. The 1b-th space reducing portion 213 may extend less in a direction toward an object than the other side of the second case 221 that is opposite to the side of the second case 221 in which the 1b-th space reducing portion 223 is formed. Accordingly, the second lens 251b may be exposed to the outside.

More specifically, when the second assembly 220 is at the first position at which it is unfolded with respect to the first assembly 210, a portion of the first acoustic module 250a exposed to the outside of the first case 211 through the first space reducing portion 213 may contact a portion of the second acoustic module 250b exposed to the outside of the second case 221 through the 1b-th space reducing portion 223.

According to the configuration, the space between the first acoustic module 250a and the second acoustic module 250b may be reduced, thereby preventing a deterioration in image quality.

Figure 9:
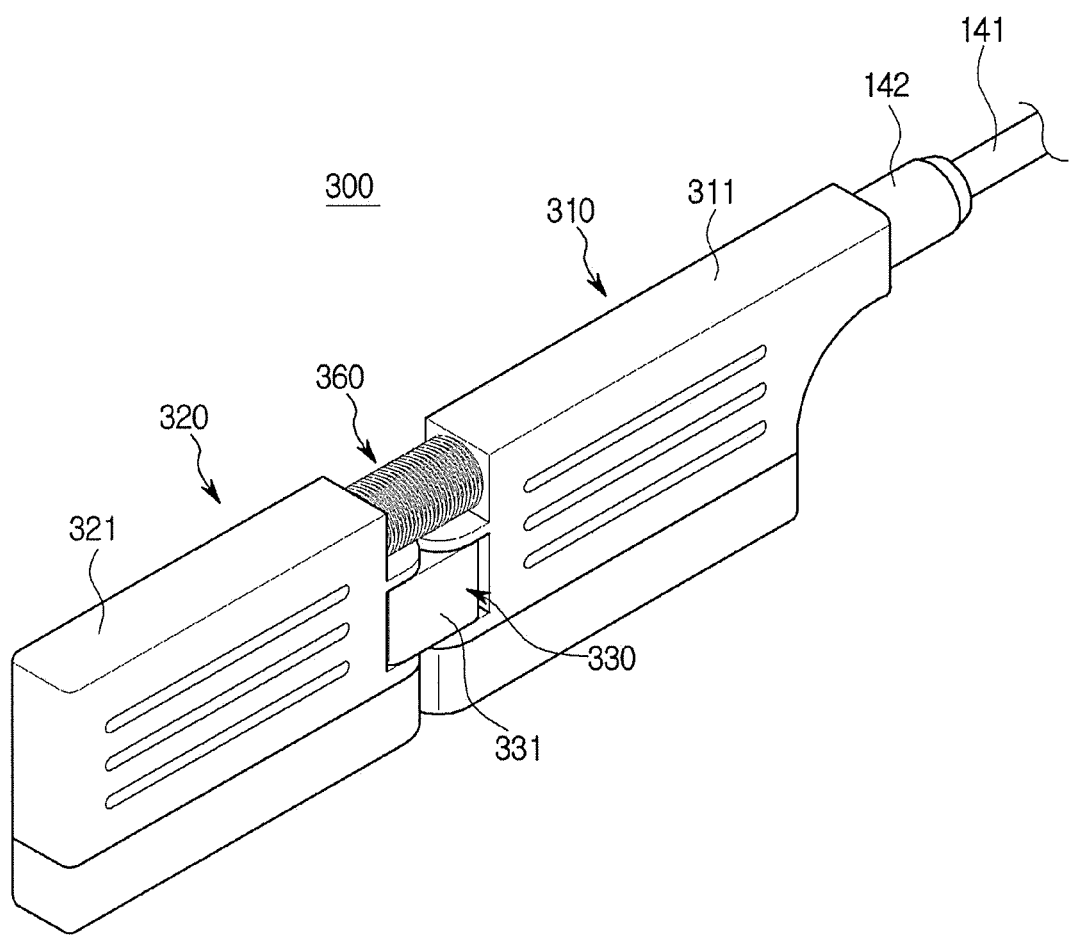
FIG. 9 shows an ultrasound probe according to another embodiment of the present disclosure when the ultrasound probe is unfolded.
Figure 10:
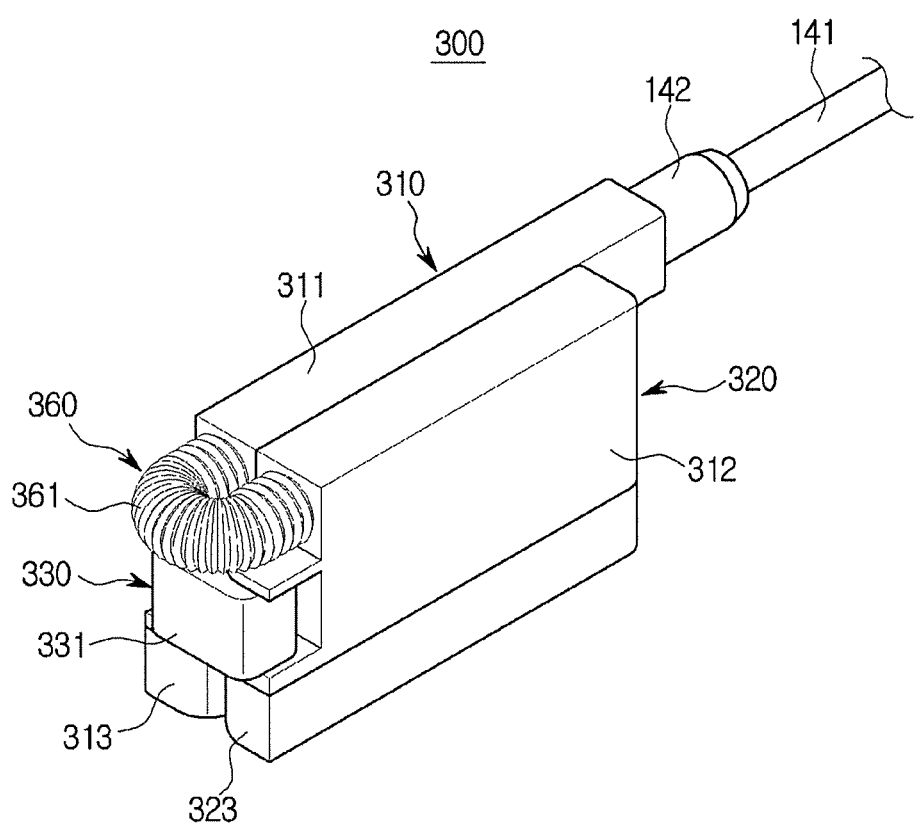
FIG. 10 shows the ultrasound probe shown in FIG. 9 when the ultrasound probe is folded.
Figure 11:
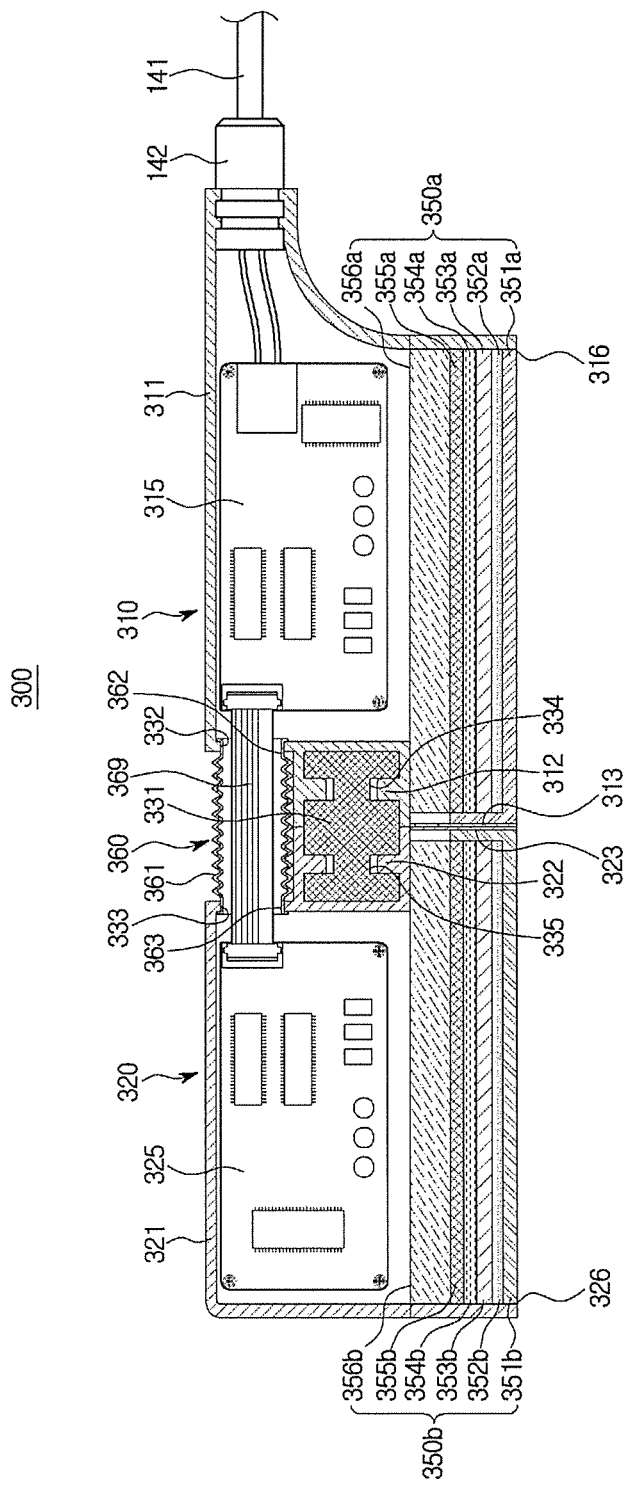
FIG. 11 shows the inside of the ultrasound probe shown in FIG. 9.

FIG. 9 shows an ultrasound probe according to another embodiment of the present disclosure when the ultrasound probe is unfolded. FIG. 10 shows the ultrasound probe shown in FIG. 9 when the ultrasound probe is folded. FIG. 11 shows the inside of the ultrasound probe shown in FIG. 9.

Referring to FIGS. 9 to 11, an ultrasound probe 300 according to another embodiment of the present disclosure will be described. In the following description, the same components as those described in the above-described embodiment will be assigned the same reference numerals, and detailed descriptions thereof will be omitted.

An ultrasound probe 300 may include a first assembly 310, a second assembly 320, and a hinge unit 330.

The first assembly 310 may include a first case 311, and in the inside of the first case 311, a first electronic component 315 and/or a first acoustic module 350a may be installed. The first case 311 may include a first lens opening 316 for exposing a first lens 351a to the outside. The first case 311 may include a 1a-th space reducing portion 313 having a thinner thickness than the other portion.

The first acoustic module 350a may include a first lens 351a, a first foreign material blocking layer 352a, a first matching layer 353a, a first piezoelectric layer 354a, a first sound-absorption layer 355a, and a first sound-reflection layer 356a.

The second assembly 320 may include a second case 321. In the inside of the second case 321, a second electric component 325 and/or a second acoustic module 350b may be installed. The second case 321 may include a second lens opening 326 for exposing a second lens 351b to the outside. The second case 321 may include a 1b-th space reducing portion 323 having a thinner thickness than the other portion.

The second acoustic module 350b may include a second lens 351b, a second foreign material blocking layer 352b, a second matching layer 353b, a second piezoelectric layer 354b, a second sound absorption layer 355b, and a second sound reflection layer 356b.

The hinge unit 330 may rotatably connect the second case 310 to the second case 320. The hinge unit 330 may include a hinge body 331.

The hinge body 331 may include a first fixing groove 334 into which a first fixing protrusion 312 is rotatably inserted. The hinge body 331 may include a second fixing groove 335 into which a second fixing protrusion 322 is rotatably inserted.

The ultrasound probe 300 according to the other embodiment of the present disclosure may include a connection member accommodating portion 360 connecting the first assembly 310 to the second assembly 320, and made of a flexible material. A connection member 369 may be accommodated in the connection member accommodating portion 360. The connection member accommodating portion 360 may stretch although the second assembly 320 rotates with respect to the first assembly 310, and maintain the connection between the first assembly 310 and the second assembly 320. The connection member accommodating portion 360 may include an accommodating portion body 361 that is stretchable.

The accommodating portion body 361 may be coupled with the first opening 332 of the first case 311 at one end, and coupled with the second opening 333 of the second case 321 at the other end. The connection member 369 may pass through a first connection opening 362 and a second connection opening 363 formed in the accommodating portion body 361 to electrically connect the first electronic component 315 to the second electronic component 325.

According to the configuration, the ultrasound probe 300 according to the other embodiment of the present disclosure may prevent the connection member 369 form being exposed to the outside.

Figure 12:
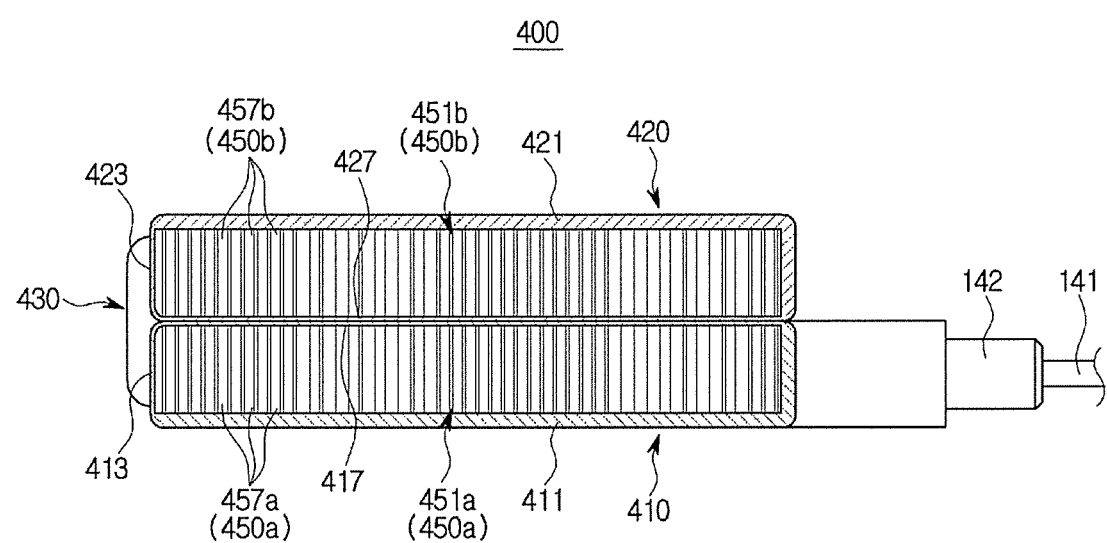
FIG. 12 shows a bottom of an ultrasound probe according to another embodiment of the present disclosure.

FIG. 12 shows a bottom of an ultrasound probe according to another embodiment of the present disclosure.

Referring to FIG. 12, an ultrasound probe 400 according to another embodiment of the present disclosure will be described. In the following description, the same components as those described in the above-described embodiment will be assigned the same reference numerals, and detailed descriptions thereof will be omitted.

The ultrasound probe 400 may include a first assembly 410, a second assembly 420, and a hinge unit 430.

The first assembly 410 may include a first case 411. In the inside of the first case 411, a first acoustic module 450a including a plurality of first elements 457a may be installed. The first acoustic module 450a may include a first lens 451a. The first case 411 may include a 1a-th space reducing portion 413.

The second assembly 420 may include a second case 421. In the inside of the second case 421, a second acoustic module 450b including a plurality of second elements 457b may be installed. The second acoustic module 450b may include a second lens 451b. The second case 421 may include a 1b-th space reducing portion 423.

The ultrasound probe 400 may inspect an object in the state in which the second assembly 420 is folded on the first assembly 410.

In order to inspect the object in the state in which the second assembly 420 is folded on the first assembly 410, the ultrasound probe 400 may include a plurality of second space reducing portions 417 and 427 at areas where which the second assembly 420 faces the first assembly 410 when the second assembly 420 is folded on the first assembly 410. The second space reducing portions 417 and 427 may include a 2a-th space reducing portion 417 and a 2b-th space reducing portion 427.

The second space reducing portions 417 and 427 may have a thinner thickness than the other portions of the first case 411 and/or the second case 421, like the first space reducing portions 113 and 123 shown in FIGS. 2 to 6. That is, the 2a-th space reducing portion 417 may have a thinner thickness than the other portion of the first case 411. The 2a-th space reducing portion 417 may have the same thickness as the 1a-th space reducing portion 413. The 2b-th space reducing portion 427 may have a thinner thickness than the other portion of the second case 421. The 2b-th space reducing portion 427 may have the same thickness as the 1b-th space reducing portion 423.

According to the configuration, the ultrasound probe 400 according to the other embodiment of the present disclosure may minimize the space between the first acoustic module 450a and the second acoustic module 450b, even when it is used in the state in which the second assembly 420 is folded on the first assembly 410, thereby preventing a deterioration in image quality.

Figure 13:
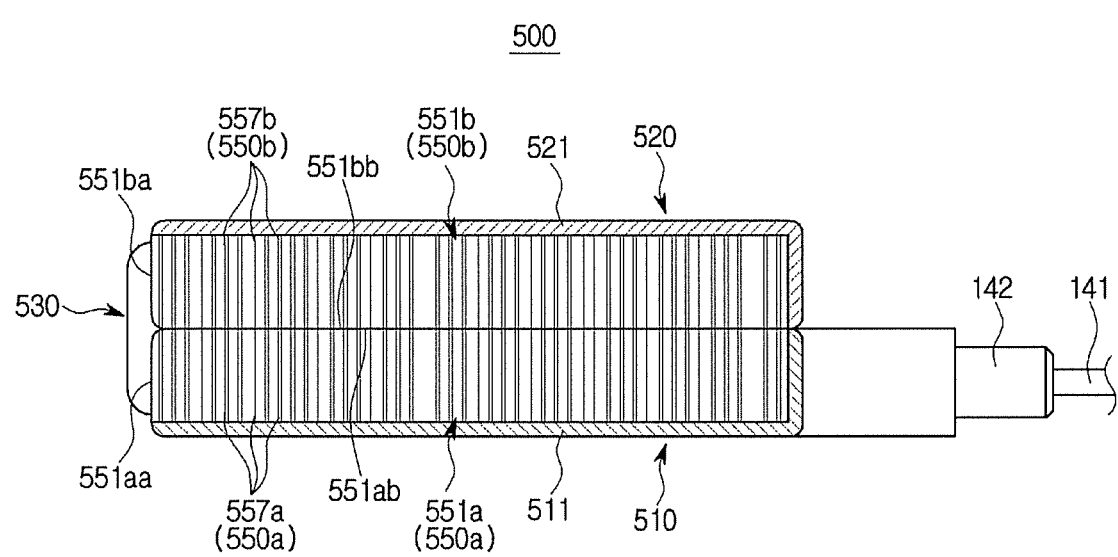
FIG. 13 shows a bottom of an ultrasound probe according to another embodiment of the present disclosure.

FIG. 13 shows a bottom of an ultrasound probe according to another embodiment of the present disclosure.

Referring to FIG. 13, an ultrasound probe 500 according to another embodiment of the present disclosure will be described. In the following description, the same components as those described in the above-described embodiment will be assigned the same reference numerals, and detailed descriptions thereof will be omitted.

An ultrasound probe 500 may include a first assembly 510, a second assembly 520, and a hinge unit 530.

The first assembly 510 may include a first case 511. In the inside of the first case 511, a first acoustic module 550a including a plurality of first elements 557a may be installed. The first acoustic module 550a may include a first lens 551a.

The first case 511 may include a 1a-th space reducing portion 511aa. The 1a-th space reducing portion 511aa may be formed in the shape of an opening in the first case 511, as the embodiment shown in FIGS. 7 and 8, to expose the first lens 551a to the outside.

The second assembly 520 may include a second case 521. In the inside of the second case 521, a second acoustic module 550b including a plurality of second elements 557b may be installed. The second acoustic module 550b may include a second lens 551b.

The second case 521 may include a 1b-th space reducing portion 511ba. The 1b-th space reducing portion 511ba may be formed in the shape of an opening in the second case 521, like the embodiment shown in FIGS. 7 and 8, to expose the second lens 551b to the outside.

The ultrasound probe 500 may inspect an object in the state in which the second assembly 520 is folded on the first assembly 510.

In order to inspect an object in the state in which the second assembly 520 is folded on the first assembly 510, the ultrasound probe 500 may include a plurality of second space reducing portions 551ab and 551bb facing each other when the second assembly 510 is folded on the first assembly 510. The second space reducing portions 551ab and 551bb may include a 2a-th space reducing portion 551ab and a 2b-th space reducing portion 551bb.

The 2a-th space reducing portion 551ab may be formed in the shape of an opening in the first case 511, like the embodiment shown in FIGS. 7 and 8, to expose a portion of the first lens 551a toward the second assembly 520.

The 2b-th space reducing portion 551bb may be formed in the shape of an opening in the second case 521, like the embodiment shown in FIGS. 7 and 8, to expose a portion of the second lens 551b toward the first assembly 510.

The portion of the first lens 551a exposed to the outside through the 2a-th space reducing portion 551ab may contact the portion of the second lens 551b exposed to the outside through the 2b-th space reducing portion 551bb.

According to the configuration, the ultrasound probe 500 according to the other embodiment of the present disclosure may minimize the space between the first acoustic module 550 and the second acoustic module 550b even when the second assembly 520 is folded on the first assembly 510, thereby preventing a deterioration in image quality.

According to a technical concept of the present disclosure, since the second assembly is rotatably connected to the first assembly, the ultrasound probe may be advantageous in view of ease of use, such as portability and storage.

According to another technical concept of the present disclosure, the ultrasound probe can minimize the distance between the first acoustic module of the first assembly and the second acoustic module of the second assembly, thereby improving image quality.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasound probe comprising:
    a first assembly;
    a second assembly coupled with the first assembly, and configured to be rotatable between a first position of being unfolded with respect to the first assembly and a second position of being folded on the first assembly;
    a first case forming an outer appearance of the first assembly;
    a second case forming an outer appearance of the second assembly;
    a first acoustic module disposed inside of the first case;
    a second acoustic module disposed inside of the second case;
    a first electronic component disposed inside of the first case and configured to drive the first acoustic module;
    a second electronic component disposed inside of the second case and configured to drive the second acoustic module; and
    a first space reducing portion configured to reduce a space between the first acoustic module and the second acoustic module when the second assembly is at the first position,
    wherein the first space reducing portion includes at least one of a 1a-th space reducing portion disposed in at least a portion of the first case toward the second assembly, and a 1b-th space reducing portion disposed in at least a portion of the second case toward the first assembly,
    wherein the 1a-th space reducing portion has a thinner thickness than other portions of the first case, and
    wherein the 1b-th space reducing portion has a thinner thickness than other portions of the second case.

2. The ultrasound probe according to claim 1, wherein the 1a-th space reducing portion exposes at least one portion of the first acoustic module to the outside of the first case, and
    wherein the 1b-th space reducing portion exposes at least one portion of the second acoustic module to the outside of the second case.

3. The ultrasound probe according to claim 2, wherein when the second assembly is at the first position, a portion of the first acoustic module exposed to the outside of the first case through the 1a-th space reducing portion contacts a portion of the second acoustic module exposed to the outside of the second case through the 1b-th space reducing portion.

4. The ultrasound probe according to claim 1, further comprising a second space reducing portion configured to reduce a space between the first acoustic module and the second acoustic module when the second assembly is at the second position,
    wherein the second space reducing portion includes at least one of a 2a-th space reducing portion disposed in at least a portion of the first case toward the second assembly, and a 2b-th space reducing portion disposed in at least a portion of the second case toward the first assembly.

5. The ultrasound probe according to claim 4, wherein the 2a-th space reducing portion has a thinner thickness than other portions of the first case, and
    wherein the 2b-th space reducing portion has a thinner thickness than other portions of the second case.

6. The ultrasound probe according to claim 4, wherein the second space reducing portion exposes at least one of the first acoustic module and the second acoustic module to the outside.

7. The ultrasound probe according to claim 1, further comprising:
    a hinge unit rotatably connecting the first assembly to the second assembly; and
    a connection member electrically connecting the first assembly to the second assembly, and passing the hinge unit.

8. The ultrasound probe according to claim 7, wherein the connection member passes a rotation shaft of the hinge unit.

9. The ultrasound probe according to claim 7, wherein the connection member comprises at least one of a Flexible Printed Circuit Board (FPCB) and a cable.

10. The ultrasound probe according to claim 1, further comprising:
    a hinge unit rotatably connecting the first assembly to the second assembly;
    a connection member accommodating portion connecting the first assembly to the second assembly, and made of a flexible material; and
    a connection member electrically connecting the first assembly to the second assembly, and disposed in the inside of the connection member accommodating portion.

11. The ultrasound probe according to claim 1, further comprising a controller configured to produce an image based on information received from at least one of the first acoustic module and the second acoustic module,
    wherein the first acoustic module comprises a plurality of first elements,
    the second acoustic module comprises a plurality of second elements,
    when the second assembly is at the first position, the controller produces an image of a space between the first assembly and the second assembly, based on a mean value of at least one first element adjacent to the second assembly among the plurality of first elements and at least one second element adjacent to the first assembly among the plurality of second elements.

* * * * *